(12) United States Patent
Higgins

(10) Patent No.: US 7,306,652 B2
(45) Date of Patent: Dec. 11, 2007

(54) SILOXANE REMOVAL PROCESS

(75) Inventor: Vincent Leo Higgins, Matthews, NC (US)

(73) Assignee: Parker-Hannifin Corporation, Cleveland, OH (US)

( * ) Notice: Subject to any disclaimer, the term of this patent is extended or adjusted under 35 U.S.C. 154(b) by 428 days.

(21) Appl. No.: 11/092,684

(22) Filed: Mar. 30, 2005

(65) Prior Publication Data

US 2006/0225571 A1 Oct. 12, 2006

(51) Int. Cl.
*B01D 53/04* (2006.01)

(52) U.S. Cl. .............. 95/97; 95/104; 95/106; 95/116; 95/148

(58) Field of Classification Search ........... 95/96–106, 95/116, 148; 96/126–128, 130
See application file for complete search history.

(56) References Cited

U.S. PATENT DOCUMENTS

| | | | |
|---|---|---|---|
| 4,000,990 A | 1/1977 | Bingham | |
| 4,770,676 A | 9/1988 | Sircar et al. | |
| 4,784,672 A | 11/1988 | Sircar | |
| 5,089,244 A | 2/1992 | Parent et al. | |
| 5,529,612 A | 6/1996 | Troost | |
| 5,900,532 A | 5/1999 | Ikeda et al. | |
| 5,922,108 A | 7/1999 | Lehmann et al. | |
| 6,196,050 B1 | 3/2001 | Ikeda et al. | |
| 6,365,108 B1 | 4/2002 | Philyaw | |
| 6,391,090 B1 | 5/2002 | Alvarez, Jr. et al. | |
| 6,444,013 B1 | 9/2002 | Helly et al. | |
| 6,461,411 B1 | 10/2002 | Watanabe et al. | |
| 6,645,898 B2 | 11/2003 | Alvarez, Jr. et al. | |
| 6,712,885 B1 | 3/2004 | Basseen et al. | |
| 2003/0097932 A1 | 5/2003 | Watanabe et al. | |
| 2004/0045440 A1 | 3/2004 | Baseen et al. | |
| 2004/0069146 A1 | 4/2004 | Carter et al. | |
| 2004/0123736 A1 | 7/2004 | Torres, Jr. et al. | |
| 2004/0168571 A1 | 9/2004 | Alvarez, Jr. et al. | |
| 2006/0000352 A1* | 1/2006 | Tower et al. ............... | 95/8 |
| 2007/0068386 A1* | 3/2007 | Mitariten ................. | 95/116 |

FOREIGN PATENT DOCUMENTS

JP 60-222144 A * 11/1985

OTHER PUBLICATIONS

Schweigkofler, Martin, et al., "Removal of siloxanes in biogases", J. Haz. Mat., B83 (2001), pp. 183-196.
Letter dated Jun. 18, 2007 from Michael J. Mitariten of Guild Associates addressed to Frank Lawrence of the United States Patent and Trademark Office with reference to the within application.
Article entitled Removal of Siloxanes in Biogases, authored by Martin Schweigkofler and Reinhard Niessner, published in the Journal of Hazardous Materials (2001), pp. 183-186.

* cited by examiner

*Primary Examiner*—Frank M. Lawrence
(74) *Attorney, Agent, or Firm*—Christopher H. Hunter

(57) ABSTRACT

Biogas released from landfills and sewage treatment plants is freed of siloxane contaminants by passing the biogas through a bed containing activated alumina, which absorbs the siloxanes. When the activated alumina becomes saturated with siloxanes, the absorption capability of the activated alumina can be recovered by passing a regeneration gas through the bed of activated alumina. A system containing two or more beds of activated alumina can use one bed to remove siloxanes from biogas while one or more of the other beds are being regenerated.

12 Claims, 11 Drawing Sheets

SILOXANE REMOVAL PROCESS

BACKGROUND OF THE INVENTION

1. Field of the Invention

The present invention relates to processes for removing silicon-containing contaminants from gases. In particular, the present invention relates to processes for removing siloxanes from biogases released from landfills and sewage treatment plants.

2. Discussion of the Background

Landfills and sewage treatment plants contain siloxanes from many sources.

One source is the semiconductor industry, which produces siloxanes as by-products of reactions involving silicon compound gases. Because siloxanes have detrimental effects on semiconductor products, siloxanes are removed from semiconductor process gases by processes such as adsorption onto diatomaceous earth, silica gel, molecular sieves and activated alumina.

The personal care industry uses volatile methyl siloxanes in products such as deodorants, tooth-pastes, skin care preparations, hair conditioners and anti-perspirants.

The cleaning industry finds many applications for siloxanes. In dry cleaning siloxanes are used as a more environmentally friendly solvent than traditional chlorofluorocarbons. In the electronics industry, siloxanes are used to clean circuitry.

Siloxane-containing waste from industrial and domestic sources is discharged into landfill sites and sewage treatment plants, along with a variety of biological organic matter.

The organic matter in the waste decomposes to produce biogas containing various volatile organic compounds, such as methane. The biogas can be used to fuel various combustion engines.

However, the biogas from landfill sites and sewage treatment plants is contaminated with siloxanes. When an engine burns siloxane-contaminated biogas, the siloxane forms precipitates of silicon dioxide. The precipitates are deposited on engine parts such as turbine blades, cylinders, heat exchangers and emission control equipment. The deposits increase the abrasion of engine surfaces, leading to a loss of engine efficiency and premature engine failure. The deposits also poison catalytic converters.

Previous attempts at removing siloxane contaminants from biogas have used adsorbents such as activated charcoal, molecular sieves and silica gel.

Improved techniques for removing siloxanes from biogas are needed.

SUMMARY OF THE INVENTION

The present invention provides a siloxane removal system for removing siloxanes from biogas emitted from landfills and sewage treatment plants. The biogas is passed through a bed containing activated alumina. Siloxane contaminants in the biogas are adsorbed on the activated alumina. When the activated alumina becomes saturated with siloxanes and loses its ability to remove siloxanes from biogas, the activated alumina is regenerated by passing a regeneration gas through the activated alumina to remove the adsorbed siloxanes. In systems containing two or more beds of activated alumina, one bed can be used to remove siloxanes from biogas while one or more of the other beds are being regenerated.

BRIEF DESCRIPTION OF THE DRAWINGS

The preferred embodiments of this invention will be described in detail with reference to the following figures.

DETAILED DESCRIPTION OF PREFERRED EMBODIMENTS

Figure 1:
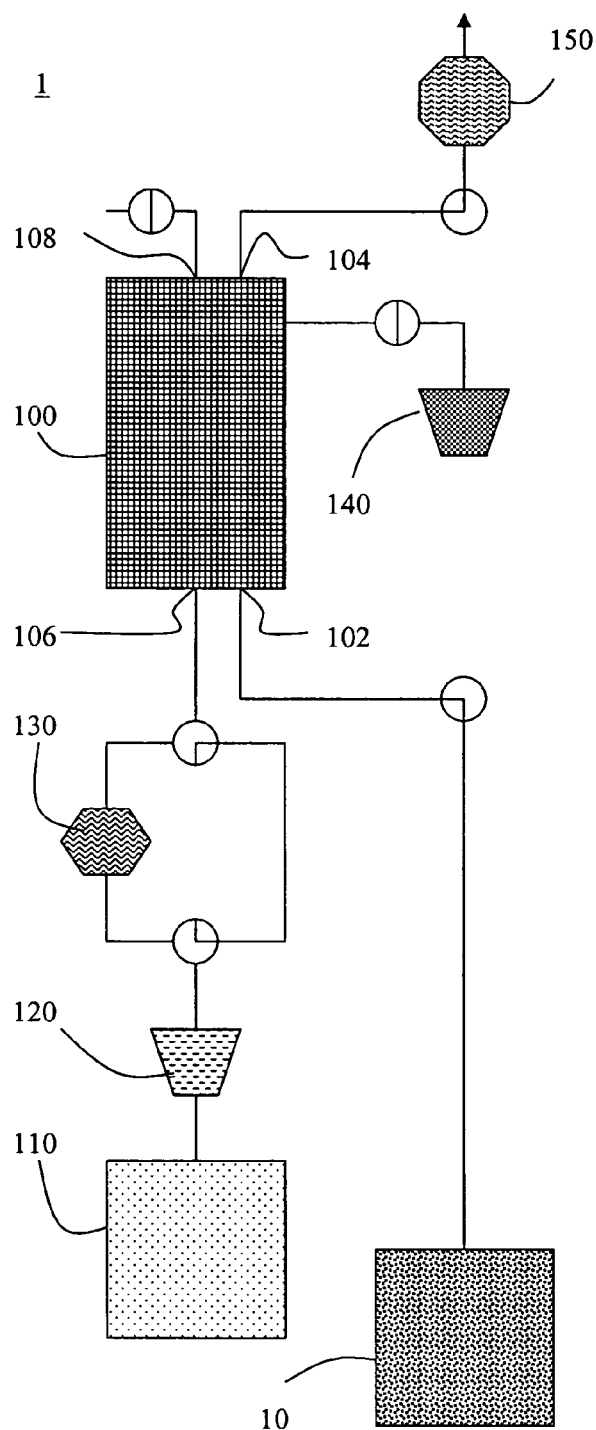
FIG. 1 is a schematic of a single bed siloxane removal system.

The present invention removes siloxane contaminates from biogas by passing the biogas through a bed containing activated alumina. The siloxanes are adsorbed onto the activated alumina, and a purified biogas leaves the bed. When the bed of activated alumina becomes saturated with siloxanes, the flow of biogas through the bed is stopped. The bed is then regenerated by passing a regeneration gas through the activated alumina and removing adsorbed siloxanes from the activated alumina.

The term "biogas" as used herein refers to a gas produced by the decomposition of organic matter. As used herein, a "biogas" can be obtained from both a landfill and a sewage treatment plant. If necessary, a pump can be used to extract and move biogas from a landfill or sewage treatment plant.

The siloxane removal system of the present invention can be made of any suitable material. To minimize corrosion when the biogas contains $H_2S$, the system can be made with 316L stainless steel.

The siloxane removal system can include one or more beds containing activated alumina. In addition to removing siloxanes, the activated alumina can act as a dessicant and remove water from the biogas. Various other biogas constituents (e.g., carbon dioxide) can also be adsorbed on the activated alumina and removed from the biogas.

The beds can include activated alumina mixed with other materials. For example, the beds can include a mixture of activated alumina and silica (e.g., the product sold under the trademark SORBEAD™).

The activated alumina can be in the form of powders, beads and pellets. Activated alumina powder can include particles having diameters in the range of from 0.0003 inches to 1.5 inches, preferably from 0.01 inches to 1 inch, more preferably from 0.1 inches to 0.5 inches.

The regeneration gas can be any gas that does not react with activated alumina. Preferably, the regeneration gas is air or nitrogen. Preferably, the regeneration gas is dry and essentially free of water. For example, the regeneration gas can be clean dry air as defined by ISO Standard 8573.1 and Quality Class 1.2.1. In embodiments, the regeneration gas can be biogas. Because biogas is not suitable for release into the environment, biogas used as regeneration gas should be vented to a flare or introduced back into the source of the biogas.

To speed regeneration, the activated alumina can be heated during regeneration. The heating of the activated alumina can be accomplished using regeneration gas that is heated before coming into contact with the activated alumina. The heating of the activated alumina can also be accomplished using electrical heaters in contact with the activated alumina. The activated alumina can be heated to a temperature in the range of from 100° F. to 250° F., preferably from 150° F. to 225° F.

A "gas mover", such as a blower, a compressor or a vacuum pump, can be used to move the regeneration gas through a bed of activated alumina. The blower and the compressor push the regeneration gas through the activated alumina. The vacuum pump pulls the regeneration gas through the activated alumina. In embodiments, two or more gas movers can be used to move the regeneration gas through the activated alumina.

Biogas from which siloxanes have been removed can be burned in various combustion engines without forming harmful silicon dioxide precipitates.

Having generally described the present invention, reference is now made to the following examples, which are provided for purposes of illustration only and are not intended to be limiting.

EXAMPLES

Example 1

Single Bed Siloxane Removal System

FIG. 1 illustrates the passage of siloxane-contaminated biogas through a single bed containing activated alumina. In FIG. 1, siloxane removal system 1 includes a single chamber 100 containing a bed comprising activated alumina. Chamber 100 includes a biogas input 102, a biogas output 104, a regeneration gas input 106 and a regeneration gas output 108. Biogas from biogas source 10 enters chamber 100 via a biogas input 102. If the pressure differential between biogas source 10 and chamber 100 does not provide a sufficient flow of biogas, the biogas can be forced from biogas source 10 into the chamber 100 by techniques well known in the art using a gas mover (not shown), such as a blower, a compressor or a vacuum pump. In chamber 100, siloxane contaminants in the biogas are adsorbed onto the activated alumina. Purified biogas then leaves chamber 100 via biogas output 104. The purified biogas can be immediately burned in biogas burner 150. Alternatively, the purified gas can be collected in a storage tank (not shown) for later use.

In embodiments, at biogas input 102 the biogas can have a pressure in a range of from 2 psig to 5000 psig, more preferably from 10 psig to 1000 psig; a temperature in a range of from 34° F. to 125° F., more preferably from 50° F. to 100° F.; and a relative humidity at 75° F. in a range of from 10% to 100% RH, more preferably from 15% to 50% RH.

When the activated alumina bed in chamber 100 has become saturated with siloxane, the activated alumina must be regenerated. To regenerate a siloxane-saturated bed of activated alumina, the bed is first isolated from the biogas source 10. Preferably the bed is then brought to atmospheric pressure conditions.

Regeneration can be accomplished in a variety of ways in which a regeneration gas is forced through the bed of siloxane-saturated activated alumina using a gas mover. In embodiments of the present invention, the gas mover is one or more of a blower, a compressor and a vacuum pump.

Figure 2:
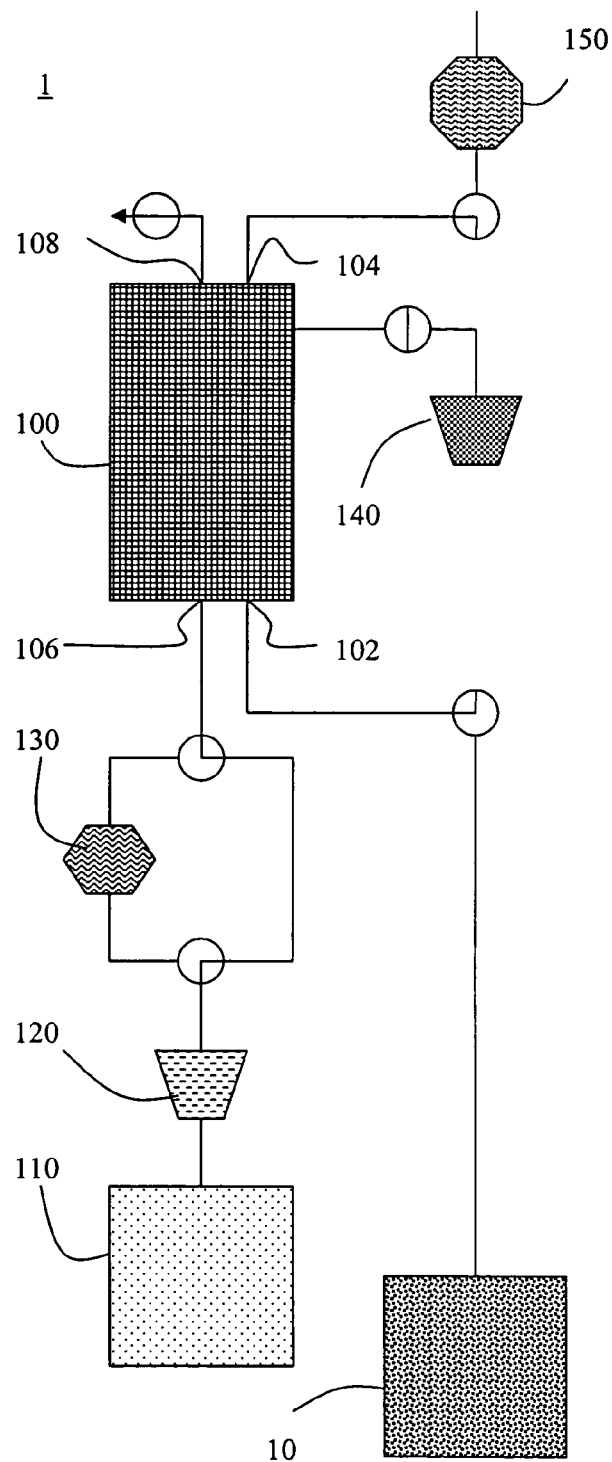
FIG. 2 is a schematic of a single bed siloxane removal system.

FIG. 2 illustrates embodiments in which the single bed system of FIG. 1 is regenerated by first disconnecting chamber 100 from biogas source 10 and then connecting chamber 100 to regeneration gas source 110. Regeneration gas from regeneration source 110 is pushed by blower 120 into chamber 100 via regeneration gas input 106. The siloxane concentration gradient between the siloxane-saturated activated alumina in chamber 100 and the regeneration gas releases adsorbed siloxanes to the regeneration gas. Preferably, the regeneration gas is blown through chamber 100 until all of the siloxane is removed from the activated alumina. Siloxane-contaminated regeneration gas leaves chamber 100 via regeneration gas output 108.

In embodiments of the present invention, the flow of the regeneration gas is nominally parallel to the flow of the biogas in the bed of activated alumina. In other embodiments the flow of the regeneration gas can be countercurrent to the flow of biogas in the bed of activated alumina.

In embodiments, at regeneration gas input 106 the regeneration gas can have a relative humidity at 75° F. in a range of from 0% to 10% RH, preferably from 0% to 5% RH.

In embodiments (not shown), biogas input 102 and regeneration gas input 106 can be the same. In other words, chamber 100 can have a single input for both the biogas and the regeneration gas.

In other embodiments (not shown), biogas output 104 and regeneration gas output 108 can be the same. In other words, chamber 100 can have a single output for both the biogas and the regeneration gas.

Figure 3:
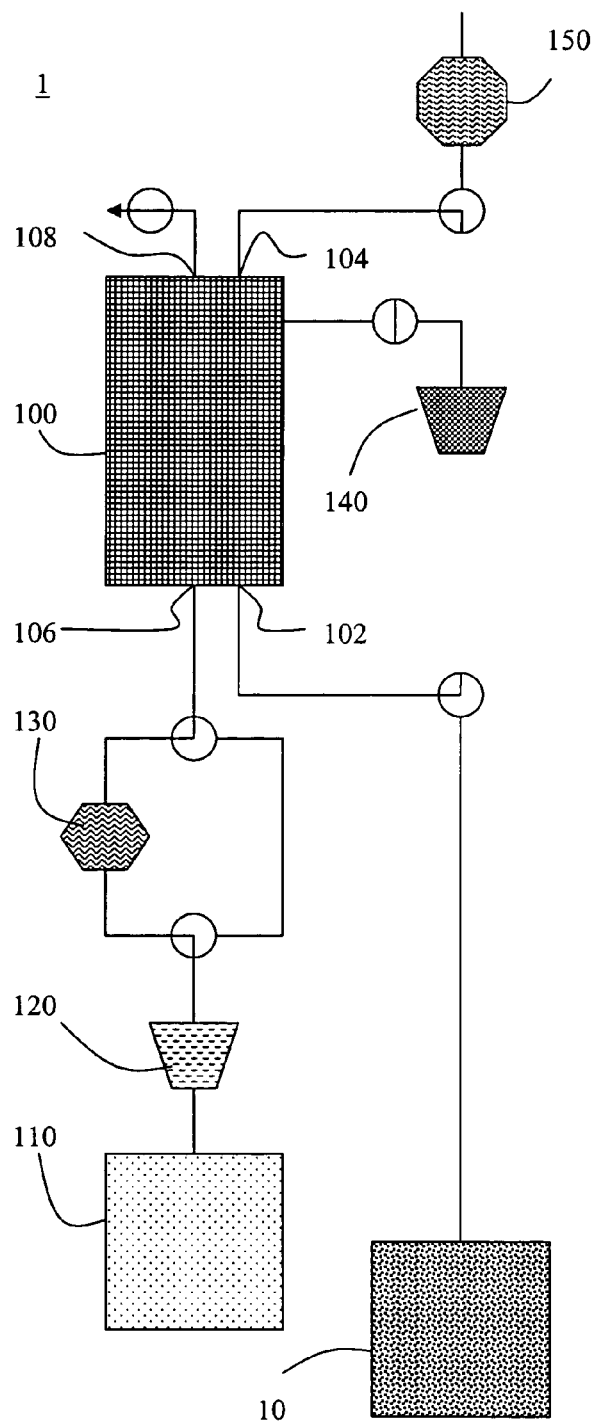
FIG. 3 is a schematic of a single bed siloxane removal system.

FIG. 3 illustrates a refinement of the embodiments of FIG. 2. In FIG. 3 the regeneration gas is pushed by blower 120 through a regeneration gas heater 130 before entering chamber 100 via regeneration gas input 106. The regeneration gas heater 130 heats the regeneration gas. Upon entering chamber 100, the heated regeneration gas heats the activated alumina and causes adsorbed siloxanes to desorb from the activated alumina into the regeneration gas. Preferably the heating is continued until all of the siloxane is removed from the activated alumina. Siloxane-contaminated regeneration gas leaves chamber 100 via regeneration gas output 108. If biogas is used as the heated regeneration gas, then the biogas exiting chamber 100 can be fed back (not shown) into biogas source 10 for reuse as a regeneration gas or for purification.

Figure 4:
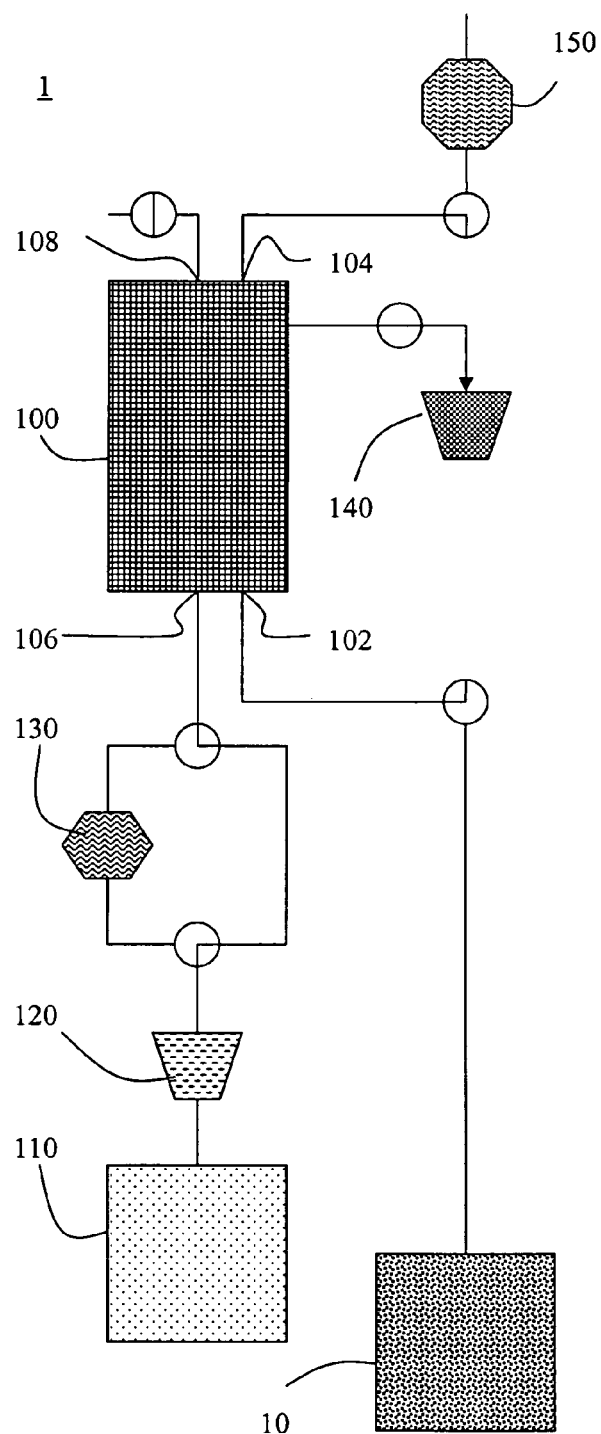
FIG. 4 is a schematic of a single bed siloxane removal system.

FIG. 4 illustrates embodiments in which the single bed system of FIG. 1 is regenerated by first isolating chamber 100 from biogas source 10 and then connecting chamber 100 to regeneration gas source 110. Regeneration gas from regeneration source 110 is pulled by vacuum pump 140 into chamber 100 via regeneration gas input 106. The siloxane concentration gradient between the siloxane-saturated activated alumina in chamber 100 and the regeneration gas releases adsorbed siloxanes to the regeneration gas. Preferably, the regeneration gas is pumped through the chamber 100 until all of the siloxane is removed from the activated alumina. Siloxane-contaminated regeneration gas leaves chamber 100 via regeneration gas output 108 and enters vacuum pump 140.

Figure 5:
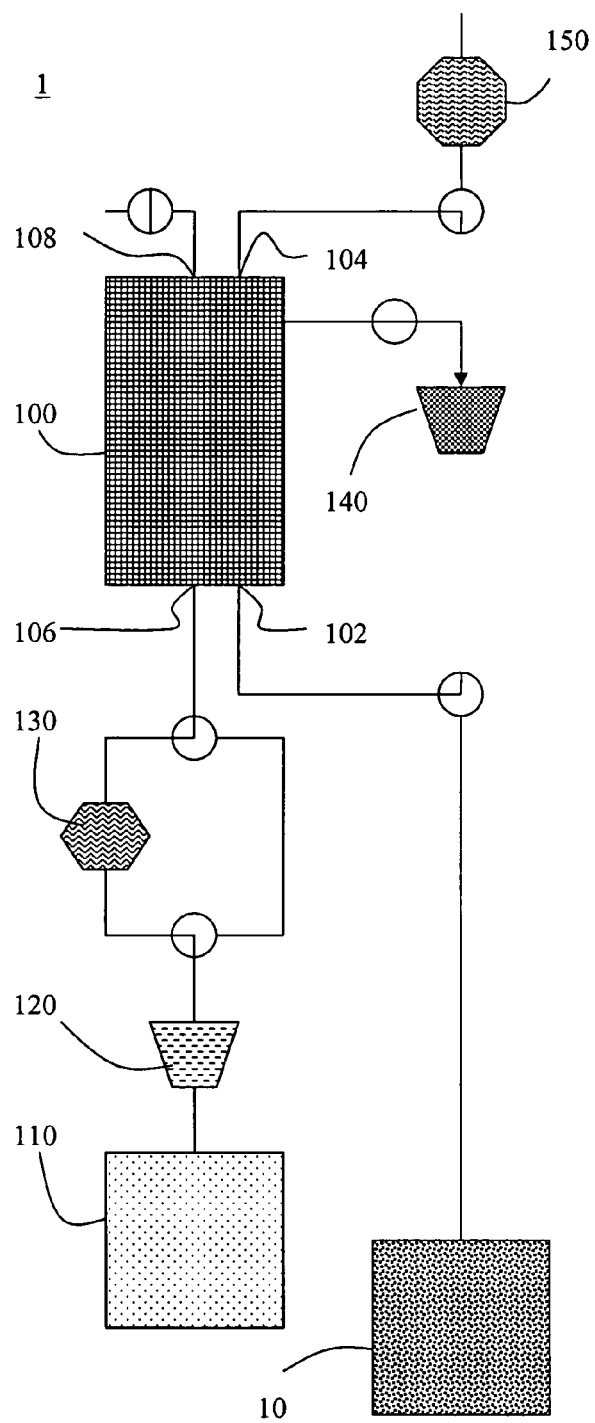
FIG. 5 is a schematic of a single bed siloxane removal system.

FIG. 5 illustrates a refinement of the embodiments of FIG. 4. In FIG. 5 the regeneration gas is pulled by vacuum pump 140 through a regeneration gas heater 130 before entering chamber 100 via regeneration gas input 106. The regeneration gas heater 130 heats the regeneration gas. Upon entering chamber 100, the heated regeneration gas heats the activated alumina and causes adsorbed siloxanes to desorb from the activated alumina into the regeneration gas. Preferably the heating is continued until all of the siloxane is removed from the activated alumina. Siloxane-contaminated regeneration gas leaves chamber 100 via regeneration gas output 108 and enters vacuum pump 140.

In the embodiments of FIGS. 2-5, after passing through chamber 100 the regeneration gas can be vented to the atmosphere or recycled (not shown) back to the regeneration gas source 110.

Using single bed siloxane removal system 1, siloxane removal and activated alumina regeneration alternate in chamber 100 to provide an intermittent flow of biogas from which siloxanes have been removed.

Example 2

Dual Bed Siloxane Removal System

Greater efficiency in removing siloxanes from biogas can be achieved using siloxane removal systems including two or more beds containing activated alumina, because one bed can be used to remove siloxanes from biogas while one or more of the other beds are being regenerated.

Figure 6:
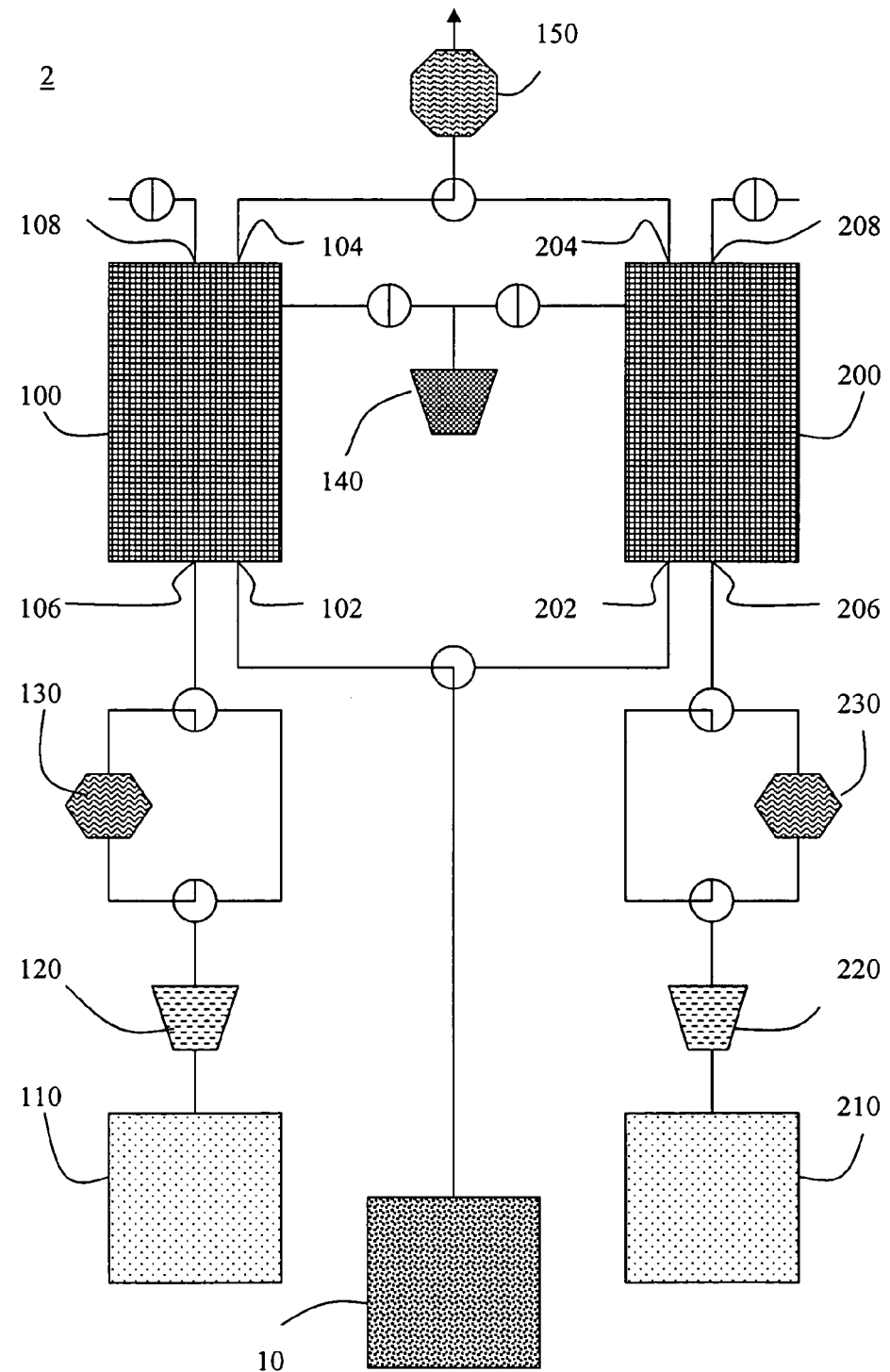
FIG. 6 is a schematic of a dual bed siloxane removal system.

FIG. 6 illustrates a two bed siloxane removal system. In FIG. 6 siloxane removal system 2 includes a chamber 100 and a chamber 200, where each chamber contains a bed comprising activated alumina. Chamber 100 includes a biogas input 102, a biogas output 104, a regeneration gas input 106 and a regeneration gas output 108. Chamber 200 includes a biogas input 202, a biogas output 204, a regeneration gas input 206 and a regeneration gas output 208. Biogas input 102 is connected to biogas input 202. Biogas output 104 is connected to biogas output 204.

Initially chamber 200 remains in stand-by mode, while biogas from biogas source 10 enters chamber 100 via a biogas input 102. If necessary, the biogas can be forced from biogas source 10 into the chamber 100 by techniques well known in the art using a gas mover (not shown), such as a blower or a vacuum pump. In chamber 100, siloxane contaminants in the biogas are adsorbed onto the activated alumina. Purified biogas then leaves chamber 100 via biogas output 104. The purified biogas can be immediately burned in biogas burner 150. Alternatively, the purified gas can be collected in a storage tank (not shown) for later use.

Eventually the activated alumina in chamber 100 becomes saturated with siloxanes and needs to be regenerated.

FIGS. 7-10 illustrate the regeneration of chamber 100 in embodiments that correspond to the single bed embodiments illustrated in FIGS. 2-5, respectively. In the embodiments of FIGS. 7-10, while chamber 100 is being regenerated the flow of biogas from biogas source 10 is redirected. The biogas is diverted from chamber 100 to chamber 200 (i.e. from biogas input 102 to biogas input 202) for removal of siloxane contaminants. At the same time the source of purified biogas to biogas burner 150 is switched from biogas output 104 of chamber 100 and to biogas output 204 of chamber 200. Means of redirecting gas flows are well known in the art and include, e.g., valves. In FIGS. 7-10, while activated alumina is being regenerated in chamber 100, siloxanes are being removed from biogas in chamber 200.

Figure 7:
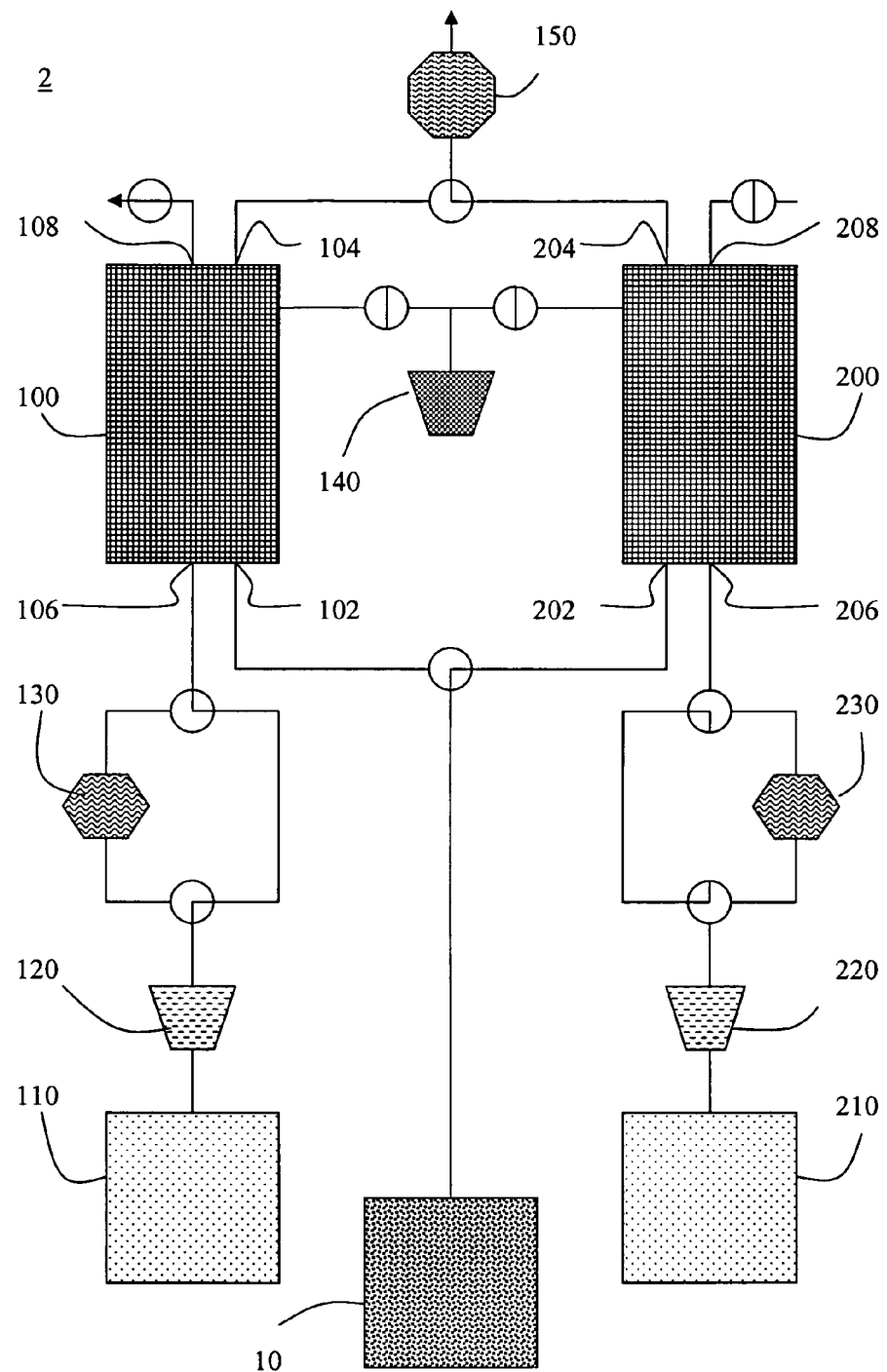
FIG. 7 is a schematic of a dual bed siloxane removal system.
Figure 8:
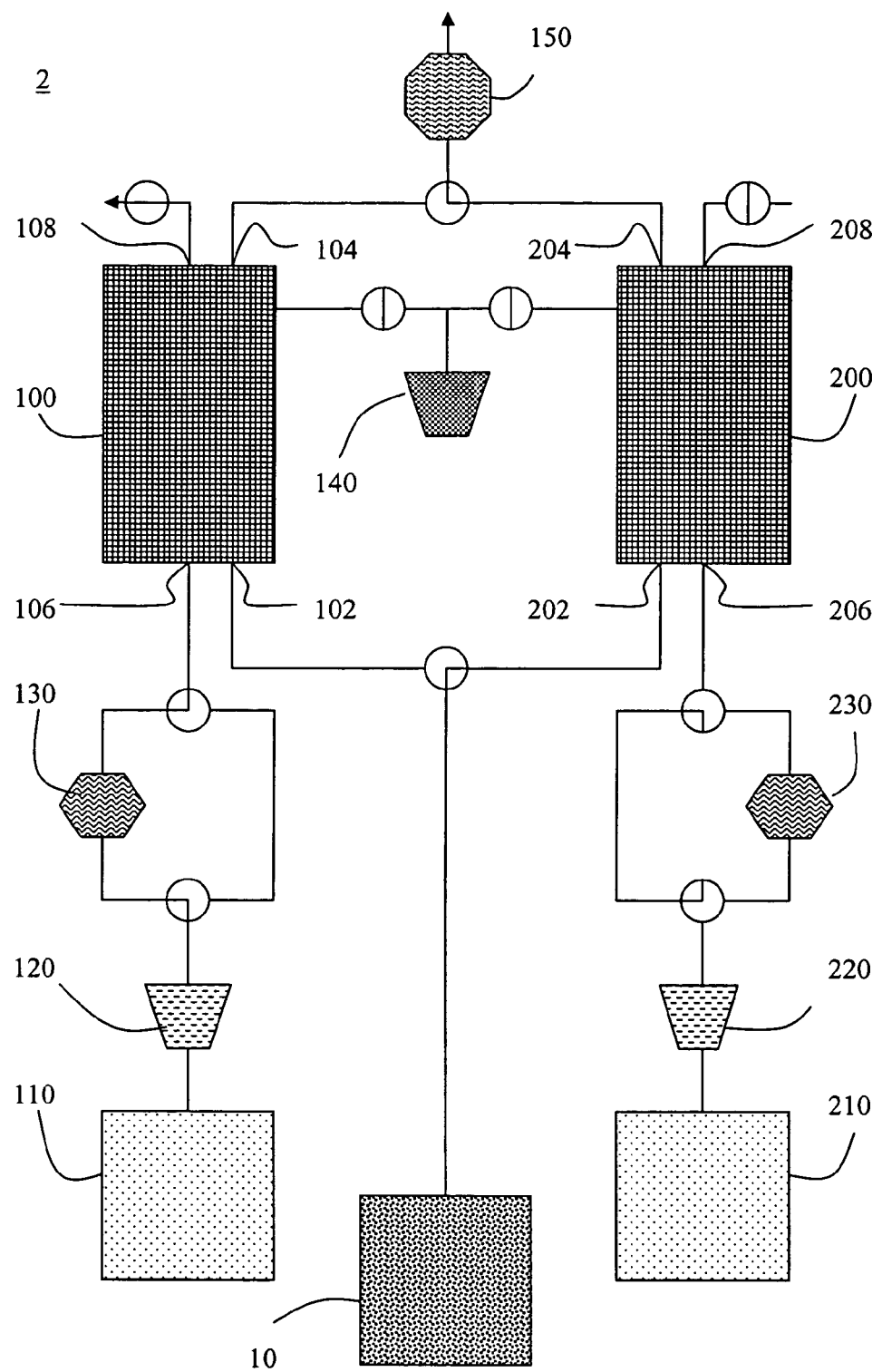
FIG. 8 is a schematic of a dual bed siloxane removal system.

In FIG. 7, regeneration of the activated alumina in chamber 100 by removal of adsorbed siloxanes is accomplished by blowing regeneration gas through chamber 100 using blower 120. In FIG. 8, the regeneration gas from blower 120 is heated by regeneration gas heater 130 before entering chamber 100.

Figure 9:
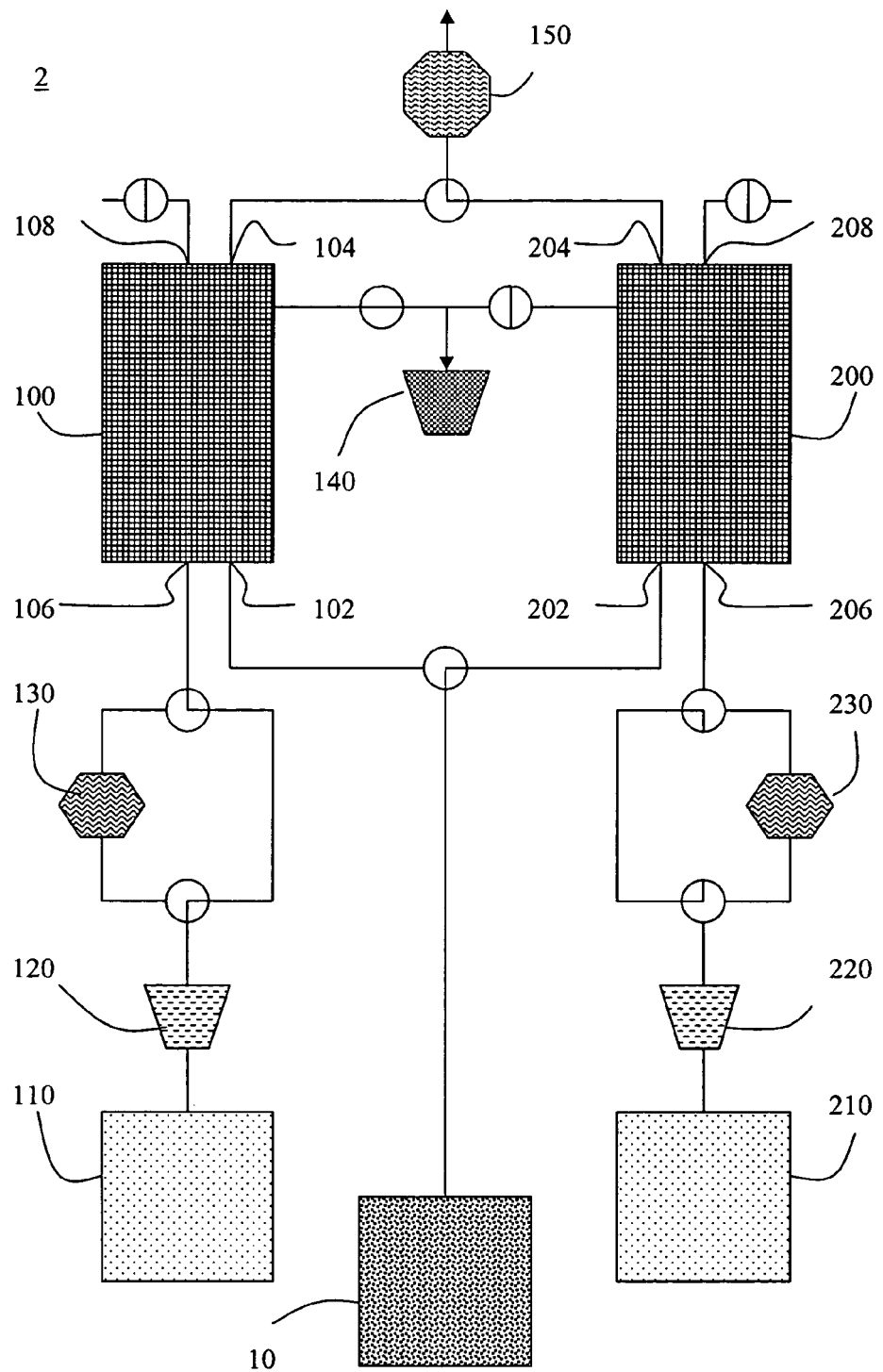
FIG. 9 is a schematic of a dual bed siloxane removal system.
Figure 10:
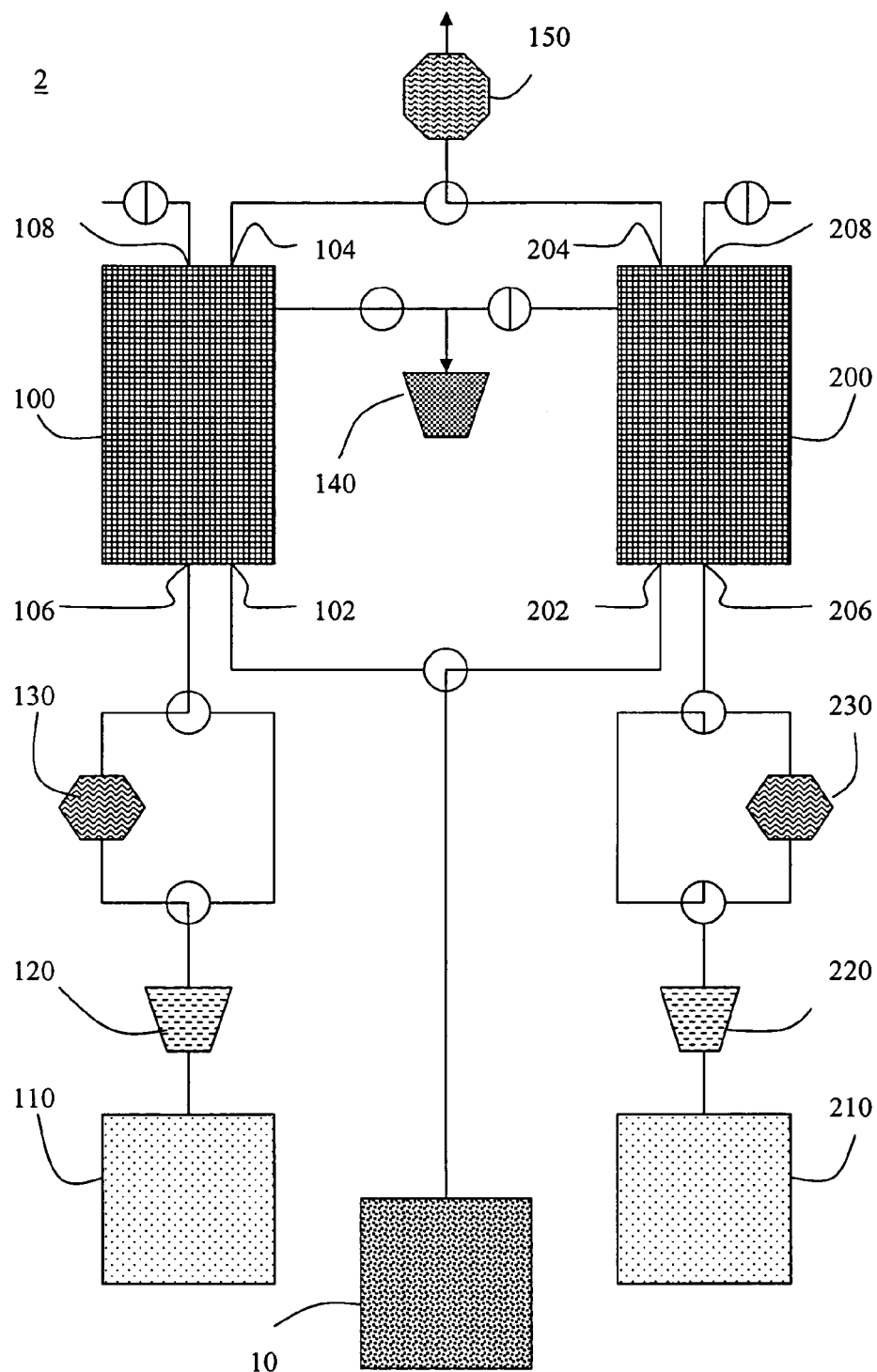
FIG. 10 is a schematic of a dual bed siloxane removal system.

In FIG. 9, regeneration of the activated alumina in chamber 100 is accomplished by pulling regeneration gas through chamber 100 using vacuum pump 140. In FIG. 10, the regeneration gas pulled by vacuum pump 140 is heated by regeneration gas heater 130 before entering chamber 100.

After the activated alumina in chamber 100 is regenerated, chamber 100 can be reconnected to biogas source 10 to remove siloxanes from biogas. At the same time chamber 200 can be disconnected from biogas source 10 and regenerated using processes analogous to those described above. In embodiments, regeneration gas can be pushed through chamber 200 using blower 220 or can be pulled through chamber 200 using vacuum pump 140. In these embodiments, the regeneration gas can be heated by regeneration gas heater 230 before entering chamber 200.

Figure 11:
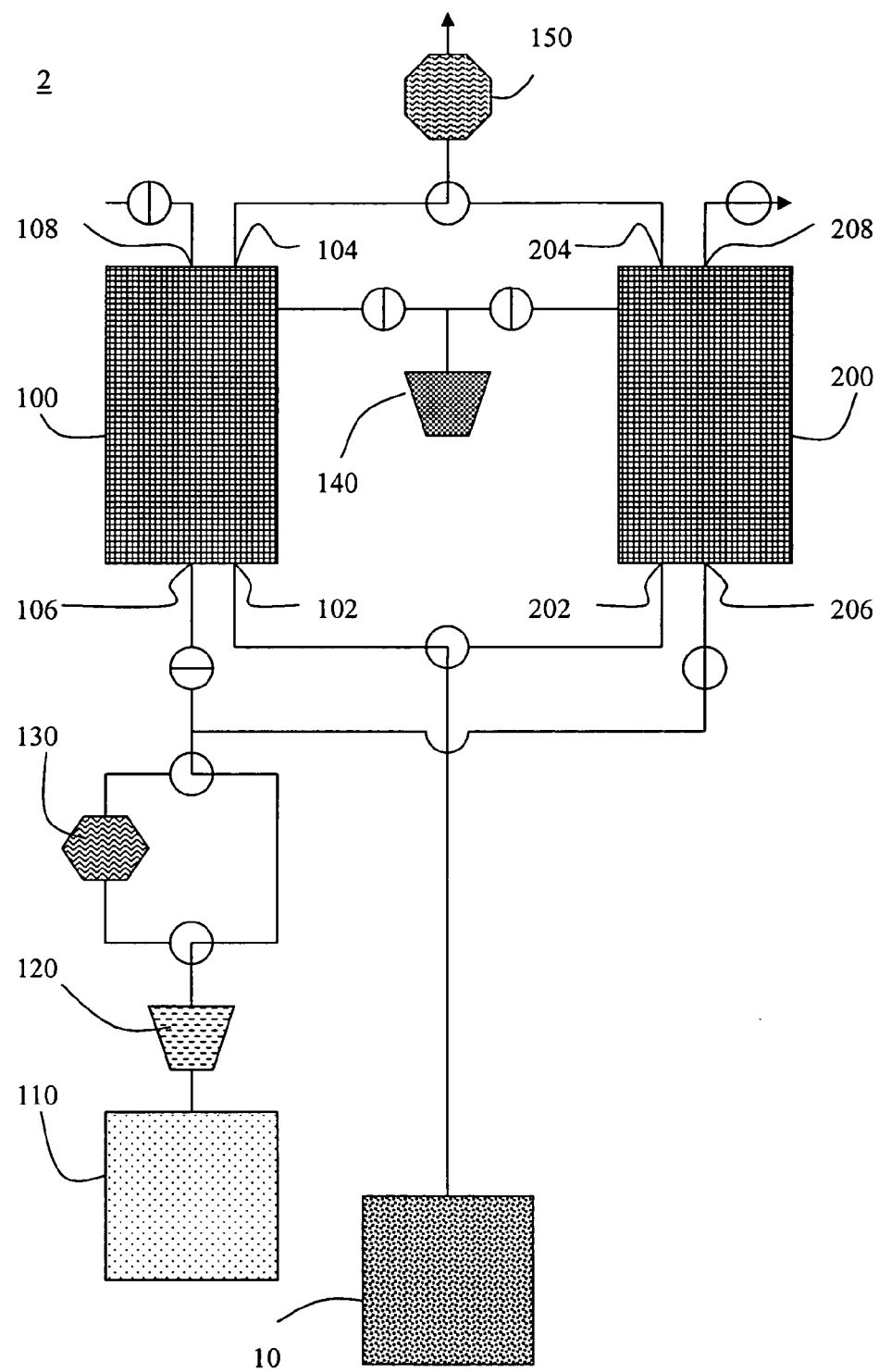
FIG. 11 is a schematic of a dual bed siloxane removal system.

In other embodiments, as illustrated in FIG. 11, the regeneration system formed by blower 120, regeneration gas heater 130 and vacuum pump 140 used to regenerate the activated alumina in chamber 100 can be used to regenerate the activated alumina in chamber 200. In particular, regeneration gas can be pushed through chamber 200 using blower 120 or can be pulled through chamber 200 used vacuum pump 140. In these other embodiments, the regeneration gas can be heated by regeneration gas heater 130 before entering chamber 200.

In still further embodiments, not shown but well within the skill in the art, three or more beds of activated alumina can be regenerated using a single regeneration system.

In even still further embodiments, not shown but well within the skill in the art, a bed of activated alumina can be regenerated using the regeneration gas from two or more regeneration systems.

In some cases activated alumina that has been heated during regeneration will have to be cooled before the regenerated activated alumina can again be used to remove siloxanes from biogas. The cooling can be accomplished by a variety of methods known in the art. For example, the hot activated alumina can be cooled by pushing with blower 120 (or blower 220), or pulling with vacuum pump 140, unheated regeneration gas through the activated alumina and venting the cooling gas to the atmosphere. A gas having a different composition than the regeneration gas (not shown) can be used as a cooling gas to cool the activated alumina. Cooling can also be accomplished by convection cooling, preferably with the regenerated activated alumina at atmospheric pressure.

Using dual bed siloxane removal system 2, siloxane removal and activated alumina regeneration can be carried out cyclically in chambers 100 and 200 to provide a continuous flow of biogas from which siloxanes have been removed.

While the present invention has been described with respect to specific embodiments, it is not confined to the specific details set forth, but includes various changes and modifications that may suggest themselves to those skilled in the art, all falling within the scope of the invention as defined by the following claims. The disclosure herein of a range of values is a disclosure of every numerical value within that range.

What is claimed is:

1. A purification process for removing siloxanes from a biogas, the process comprising obtaining from a landfill or sewage treatment plant a biogas comprising siloxanes;

passing the biogas through a bed comprising activated alumina;

adsorbing onto the activated alumina at least a portion of the siloxanes in the biogas; and regenerating the activated alumina by removing from the activated alumina at least a portion of the siloxanes adsorbed on the activated alumina.

2. The process according to claim 1, wherein the regenerating comprises heating the activated alumina.

3. The process according to claim 1, wherein the regenerating comprising exposing the activated alumina to a vacuum.

4. The process according to claim 3, further comprising heating the activated alumina while the activated alumina is exposed to the vacuum.

5. The process according to claim 1, wherein the regenerating comprises passing a regeneration gas through the bed.

6. The process according to claim 5, further comprising heating the regeneration gas before passing the regeneration gas through the bed.

7. The process according to claim 5, wherein the regeneration gas comprises the biogas.

8. The process according to claim 5, wherein the regeneration gas is selected from the group consisting of air and nitrogen.

9. The process according to claim 1, wherein the bed containing activated alumina is a first bed;

during the regenerating of the activated alumina in the first bed the biogas is passed through a second bed containing activated alumina; and the process further comprises adsorbing onto the activated alumina in the second bed at least a portion of the siloxanes in the biogas.

10. The process according to claim 9, further comprising regenerating the activated alumina in the second bed by removing from the activated alumina in the second bed at least a portion of the siloxanes adsorbed on the activated alumina in the second bed.

11. The process according to claim 1, wherein the bed further comprises silica.

12. The process according to claim 1, wherein the activated alumina is selected from the group consisting of powder, beads and pellets.

* * * * *